United States Patent
Bailey et al.

(10) Patent No.: US 8,709,765 B2
(45) Date of Patent: Apr. 29, 2014

(54) MANIPULATION OF AN ALTERNATIVE RESPIRATORY PATHWAY IN PHOTO-AUTOTROPHS

(75) Inventors: Shaun Bailey, Los Altos, CA (US);
Bertrand Vick, Emeryville, CA (US);
Jeff Moseley, Redwood City, CA (US)

(73) Assignee: Aurora Algae, Inc., Hayward, CA (US)

( * ) Notice: Subject to any disclaimer, the term of this patent is extended or adjusted under 35 U.S.C. 154(b) by 83 days.

(21) Appl. No.: 12/840,269

(22) Filed: Jul. 20, 2010

(65) Prior Publication Data

US 2011/0059495 A1 Mar. 10, 2011

Related U.S. Application Data

(60) Provisional application No. 61/227,026, filed on Jul. 20, 2009.

(51) Int. Cl.
| | |
|---|---|
| C12P 7/64 | (2006.01) |
| C12N 1/12 | (2006.01) |
| C12N 15/00 | (2006.01) |
| C12N 15/74 | (2006.01) |
| C12N 9/02 | (2006.01) |

(52) U.S. Cl.
USPC .............. 435/134; 435/257.1; 435/257.2; 435/320.1; 435/471; 435/477; 435/189

(58) Field of Classification Search
USPC ........ 435/134, 257.1, 257.2, 320.1, 471, 477, 435/189
See application file for complete search history.

(56) References Cited

U.S. PATENT DOCUMENTS

| | | | |
|---|---|---|---|
| 1,926,780 A | 9/1933 | Lippincott | |
| 3,468,057 A | 9/1969 | Buisson et al. | |
| 3,962,466 A | 6/1976 | Nakabayashi | |
| 4,003,337 A | 1/1977 | Moore | |
| 4,267,038 A | 5/1981 | Thompson | |
| 4,365,938 A | 12/1982 | Warinner | |
| 4,535,060 A | 8/1985 | Comai | |
| 4,658,757 A | 4/1987 | Cook | |
| 5,105,085 A | 4/1992 | McGuire et al. | |
| 5,478,208 A | 12/1995 | Kasai et al. | |
| 5,527,456 A | 6/1996 | Jensen | |
| 5,661,017 A | 8/1997 | Dunahay et al. | |
| 5,668,298 A | 9/1997 | Waldron et al. | |
| 5,723,595 A | 3/1998 | Thompson et al. | |
| 5,823,781 A | 10/1998 | Hitchcock et al. | |
| 6,027,900 A | 2/2000 | Allnutt et al. | |
| 6,117,313 A | 9/2000 | Goldman et al. | |
| 6,143,562 A | 11/2000 | Trulson et al. | |
| 6,166,231 A | 12/2000 | Hoeksema | |
| 6,297,054 B1 | 10/2001 | Maliga et al. | |
| 6,372,460 B1 | 4/2002 | Gladue et al. | |
| 6,448,055 B1 | 9/2002 | Shimizu et al. | |
| 6,736,572 B2 | 5/2004 | Geraghty | |
| 6,750,048 B2 | 6/2004 | Ruecker et al. | |
| 6,831,040 B1 | 12/2004 | Unkefer et al. | |
| 6,871,195 B2 | 3/2005 | Ryan et al. | |
| 7,244,609 B2 | 7/2007 | Drocourt et al. | |
| 7,381,326 B2 | 6/2008 | Haddas | |
| 7,410,637 B2 | 8/2008 | Sayre et al. | |
| 7,449,568 B2 | 11/2008 | Fukuda et al. | |
| 7,547,551 B2 | 6/2009 | Schuler et al. | |
| 8,039,230 B2 * | 10/2011 | Otte et al. | 435/69.1 |
| 8,119,859 B2 | 2/2012 | Vick et al. | |
| 8,314,228 B2 | 11/2012 | Kilian et al. | |
| 8,318,482 B2 | 11/2012 | Vick et al. | |
| 2003/0049720 A1 | 3/2003 | Hoshino et al. | |
| 2003/0140021 A1 | 7/2003 | Ryan et al. | |
| 2003/0143743 A1 | 7/2003 | Schuler et al. | |
| 2003/0199490 A1 | 10/2003 | Antoni-Zimmermann et al. | |
| 2003/0211089 A1 | 11/2003 | Sayre et al. | |
| 2004/0161364 A1 | 8/2004 | Carlson | |
| 2004/0262219 A1 | 12/2004 | Jensen | |
| 2005/0064577 A1 | 3/2005 | Berzin | |
| 2005/0095569 A1 | 5/2005 | Franklin | |
| 2005/0124010 A1 | 6/2005 | Short et al. | |

(Continued)

FOREIGN PATENT DOCUMENTS

| | | |
|---|---|---|
| CN | 1627764 | 6/2005 |
| CN | 1867140 | 11/2006 |
| CN | 1956335 | 5/2007 |
| CN | 101289659 | 10/2008 |
| WO | 2004106238 A2 | 12/2001 |
| WO | 2007084078 | 7/2007 |
| WO | 2008060571 A2 | 5/2008 |
| WO | 2008106803 A1 | 9/2008 |
| WO | 2008060571 A3 | 11/2008 |
| WO | 2008060571 A8 | 2/2009 |
| WO | 2009124070 A1 | 10/2009 |
| WO | 2009149470 A1 | 12/2009 |
| WO | 2010011335 A1 | 1/2010 |
| WO | 2011011463 A2 | 1/2011 |
| WO | 2011049995 A1 | 4/2011 |

OTHER PUBLICATIONS

Broun et al., Catalytic plasticity of fatty acid modification enzymes underlying chemical diversity of plant lipids. Science, 1998, vol. 282: 1315-1317.*

(Continued)

*Primary Examiner* — Ganapathirama Raghu
(74) *Attorney, Agent, or Firm* — Carr & Ferrell LLP (57) ABSTRACT

Exemplary methods for increasing TAG production in an algal cell during imbalanced growth conditions are provided. Some methods comprise knocking out an AOX gene, wherein the AOX gene produces an amino acid sequence having substantial similarity to the amino acid sequence of SEQ. ID. NO. 2. In further methods, the algal cell may be of genus *Nannochloropsis*. The AOX gene may be replaced by a construct having a nucleotide sequence having substantial similarity to SEQ ID. NOS. 3 through 5 (inclusive), wherein each of the sequences are next to or in close proximity to one another in a linear fashion. In some methods, the AOX gene may be replaced via homologous recombination. As a result, lipid production by the selected recombinant algal cell may be increased over that produced by a wild-type algal cell.

10 Claims, 9 Drawing Sheets

(56) References Cited

U.S. PATENT DOCUMENTS

| | | | |
|---|---|---|---|
| 2005/0170479 | A1 | 8/2005 | Weaver et al. |
| 2005/0181345 | A1 | 8/2005 | Bradbury et al. |
| 2005/0260553 | A1 | 11/2005 | Berzin |
| 2006/0031087 | A1 | 2/2006 | Fox et al. |
| 2006/0044259 | A1 | 3/2006 | Hotelling et al. |
| 2006/0045750 | A1 | 3/2006 | Stiles |
| 2006/0101535 | A1 | 5/2006 | Forster et al. |
| 2006/0122410 | A1 | 6/2006 | Fichtali et al. |
| 2006/0155558 | A1 | 7/2006 | Corpening |
| 2006/0166243 | A1 | 7/2006 | Su et al. |
| 2006/0166343 | A1 | 7/2006 | Hankamer et al. |
| 2006/0192690 | A1 | 8/2006 | Philipp |
| 2007/0178451 | A1 | 8/2007 | Deng et al. |
| 2008/0118964 | A1 | 5/2008 | Huntley et al. |
| 2008/0120749 | A1 | 5/2008 | Melis et al. |
| 2008/0160488 | A1 | 7/2008 | Younkes et al. |
| 2008/0160591 | A1 | 7/2008 | Willson et al. |
| 2008/0194029 | A1 | 8/2008 | Hegemann et al. |
| 2008/0268539 | A1 | 10/2008 | Singh et al. |
| 2008/0293132 | A1 | 11/2008 | Goldman et al. |
| 2009/0029445 | A1 | 1/2009 | Eckelberry et al. |
| 2009/0061493 | A1 | 3/2009 | Trimbur et al. |
| 2009/0061928 | A1 | 3/2009 | Lee et al. |
| 2009/0148931 | A1 | 6/2009 | Wilkerson et al. |
| 2009/0234146 | A1 | 9/2009 | Cooney et al. |
| 2009/0317857 | A1 | 12/2009 | Vick et al. |
| 2009/0317878 | A1 | 12/2009 | Champagne et al. |
| 2009/0317904 | A1 | 12/2009 | Vick et al. |
| 2009/0319338 | A1 | 12/2009 | Parks et al. |
| 2009/0325270 | A1 | 12/2009 | Vick et al. |
| 2010/0068772 | A1 | 3/2010 | Downey |
| 2010/0100520 | A1 | 4/2010 | Dargue et al. |
| 2010/0198659 | A1 | 8/2010 | Meltzer et al. |
| 2010/0210003 | A1 | 8/2010 | King et al. |
| 2010/0210832 | A1 | 8/2010 | Kilian et al. |
| 2010/0314324 | A1 | 12/2010 | Rice et al. |
| 2010/0323387 | A1 | 12/2010 | Bailey et al. |
| 2010/0330643 | A1 | 12/2010 | Kilian et al. |
| 2011/0015415 | A1 | 1/2011 | Singh et al. |
| 2011/0059495 | A1 | 3/2011 | Bailey et al. |
| 2011/0091977 | A1 | 4/2011 | Kilian et al. |
| 2012/0190115 | A1 | 7/2012 | Kilian et al. |
| 2013/0102040 | A1 | 4/2013 | Radakovits et al. |
| 2013/0131330 | A1 | 5/2013 | Kilian et al. |

OTHER PUBLICATIONS

Kisselev L., Polypeptide release factors in prokaryotes and eukaryotes: same function, different structure. Structure, 2002, vol. 10: 8-9.*

Wishart et al., A single mutation converts a novel phosphotyrosine binding domain into a dual-specificity phosphatase. J. Biol. Chem., 1995, vol. 270(45): 26782-26785.*

Whisstock et al., Prediction of protein function from protein sequence. Q. Rev. Biophysics., 2003, vol. 36 (3): 307-340.*

Witkowski et al., Conversion of b-ketoacyl synthase to a Malonyl Decarboxylase by replacement of the active cysteine with glutamine. Biochemistry, 1999, vol. 38: 11643-11650.*

Molnar et al. Highly specific gene silencing by artificial microRNAs in the unicellular alga *Chlamydomonas reinhardtii*. Plant Jour. ePub Jan. 17, 2009 vol. 58 No. 1 pp. 157-164. Especially abstract.

Chen et al. Conditional Production of a Functional Fish Growth Hormonal in the Transgenic Line of *Nannochloropsis oculata* (Eustigmatophyceae). J. Phycol. Jun. 2008 vol. 44 No. 3 pp. 768-776. Especially abstract.

Nelson et al. Targeted Disruption of the NIT8 Gene in *Chlamydomonas reinhardtii*. Mol. Cell Bio. Oct. 1995, vol. 15, No. 10, pp. 5762-5769. Especially abstract and p. 5763 left col. para 2.

Prein et al., "A Novel Strategy for Constructing N-terminal Chromosomal Fusions to Green Fluorescent Protein in the Yeast *Saccharomyces cerevisiae*," FEBS Letters 485 (2000) 29-34.

Wendland et al., "PCR-Based Methods Facilitate Targeted Gene Manipulations and Cloning Procedures," Curr. Gen. (2003) 44: 115-123.

Kindle, et al., "Stable Nuclear Transformation of *Chlamydomonas* Using the *Chlamydomonas* Gene for Nitrate Reductase," The Journal of Cell Biology 109(6, part 1): 2589-2601, 1989.

Endo et al., "Inactivation of Blasticidin S by *Bacillus cereus* II. Isolation and Characterization of a Plasmid, pBSR 8, From *Bacillus cereus*," The Journal of Antibiotics 41(2): 271-273 (1988).

Schiedlmeier et al., "Nuclearn Transformation of *Volvox carteri*," Proceedings of the National Academy of Sciences USA 91(11): 5080-5084 (May 1994).

Hallmann et al., "Genetic Engineering of the Multicellular Green Alga Volvox: A Modified and Multiplied Bacterial Antibiotic Resistance Gene as a Dominant Selectable Marker," The Plant Journal 17(1): 99-109 (Jan. 1999).

Office Action, Mailed Dec. 2, 2010, U.S. Appl. No. 12/220,688, filed Jul. 24, 2008.

Final Office Action, Mailed Jul. 12, 2011, U.S. Appl. No. 12/220,688, filed Jul. 24, 2008.

Advisory Action, Mailed Sep. 23, 2011, U.S. Appl. No. 12/220,688, filed Jul. 24, 2008.

Office Action, Mailed Jul. 22, 2011, U.S. Appl. No. 12/480,635, filed Jun. 8, 2009.

Final Office Action, Mailed Jan. 31, 2012, U.S. Appl. No. 12/480,635, filed Jun. 8, 2009.

Final Office Action, Mailed Apr. 6, 2012, U.S. Appl. No. 12/480,635, filed Jun. 8, 2009.

Notice of Allowance, Mailed Jul. 19, 2012, U.S. Appl. No. 12/480,635, filed Jun. 8, 2009.

Notice of Allowance, Mailed Aug. 27, 2012, U.S. Appl. No. 12/480,635, filed Jun. 8, 2009.

Office Action, Mailed Feb. 9, 2012, U.S. Appl. No. 12/492,077, filed Jun. 25, 2009.

Final Office Action, Mailed Oct. 9, 2012, U.S. Appl. No. 12/492,077, filed Jun. 25, 2009.

Office Action, Mailed Aug. 29, 2011, U.S. Appl. No. 12/706,683, filed Feb. 16, 2010.

Final Office Action, Mailed May 2, 2012, U.S. Appl. No. 12/706,683, filed Feb. 16, 2010.

Notice of Allowance, Mailed Jul. 13, 2012, U.S. Appl. No. 12/706,683, filed Feb. 16, 2010.

Final Office Action, Mailed Jun. 3, 2011, U.S. Appl. No. 12/581,812, filed Oct. 19, 2009.

Office Action, Mailed Apr. 5, 2013, U.S. Appl. No. 12/581,812, filed Oct. 19, 2009.

Office Action, Mailed May 23, 2012, U.S. Appl. No. 12/488,106, filed Jun. 19, 2009.

Final Office Action, Mailed Mar. 14, 2013, U.S. Appl. No. 12/488,106, filed Jun. 19, 2009.

Notice of Allowance, Mailed Jul. 22, 2011, U.S. Appl. No. 12/480,611, filed Jun. 8, 2009.

Notice of Allowance, Mailed Oct. 18, 2011, U.S. Appl. No. 12/480,611, filed Jun. 8, 2009.

Office Action, Mailed Jan. 30, 2013, U.S. Appl. No. 13/011,809, filed Jan. 21, 2011.

Notice of Allowance, Mailed Aug. 23, 2013, U.S. Appl. No. 13/011,809, filed Jan. 21, 2011.

Notice of Allowance, filed Oct. 3, 2012, U.S. Appl. No. 13/458,914, filed Apr. 27, 2012.

Notice of Allowance, Mailed Jan. 14, 2013, U.S. Appl. No. 13/458,914, filed Apr. 27, 2012.

Office Action, Mailed Jul. 10, 2013, U.S. Appl. No. 13/459,215, filed Apr. 29, 2012.

Office Action, Mailed Jul. 23, 2012, U.S. Appl. No. 13/372,467, filed Feb. 13, 2012.

Final Office Action, Mailed Mar. 13, 2013, U.S. Appl. No. 13/372,467, filed Feb. 13, 2012.

Notice of Allowance, Mailed Apr. 29, 2013, U.S. Appl. No. 13/685,659, filed Nov. 26, 2012.

Notice of Allowance, Mailed Aug. 2, 2013, U.S. Appl. No. 13/685,659, filed Nov. 26, 2012.

International Search Report, Mailed Sep. 16, 2009, PCT/US2009/004296, Filed Jul. 24, 2009.

International Search Report, Mailed Oct. 30, 2009, PCT/US2009/046656, Filed Jun. 8, 2009.

(56) References Cited

OTHER PUBLICATIONS

International Search Report, Mailed Aug. 12, 2009, PCT/US2009/003819, Filed Jun. 25, 2009.
Extended European Search Report, Mailed Mar. 19, 2013, 10825551.4, Filed Oct. 19, 2010.
Extended European Search Report, Mailed Oct. 19, 2011, 9759628.2, Filed Jun. 8, 2009.
Office Action, Mailed Apr. 29, 2013, 9759628.2, Filed Jun. 8, 2009.
International Search Report, Mailed Oct. 20, 2010, PCT/US2010/001754, Filed Jun. 16, 2010.
International Search Report, Mailed Sep. 9, 2009, PCT/US2009/046650, Filed Jun. 8, 2009.
International Search Report, Mailed Jun. 15, 2011, PCT/US2010/042666, Filed Jul. 20, 2010.
International Search Report, Mailed Oct. 16, 2012, PCT/US2012/035633, Filed Apr. 27, 2012.
International Search Report, Mailed Sep. 13, 2013, PCT/US2013/038939, Filed Apr. 30, 2013.
Santin-Montanya, I. "Optimal Growth of *Dunaliella primolecta* in Axenic Conditions to Assay Herbicides," Chemosphere, 66, Elsevier 2006, p. 1315-1322.
Felix, R. "Use of the cell wall-less alga *Dunaliella bioculata* in herbicide screening tests," Annals of Applied Biology, 113, 1988, pp. 55-60.
Janssen, M. "Phytosynthetic efficiency of *Dunaliella tertiolecta* under short light/dark cycles," Enzyme and Microbial Technology, 29, 2001, p. 298-305.
Saenz, M.E., "Effects of Technical Grade and a Commercial Formulation of Glyphosate on Algal Population Growth," Bulletin of Environmental Contamination Toxicology, 1997, 59: pates 638-644.
Christy et al., "Effects of Glyphosate on Growth of *Chlorella*," Weed Science, vol. 29, Issue 1, Jan. 1981, pp. 5-7.
Roessler et al., "Genetic Engineering Approaches for Enhanced Production of Biodiesel Fuel from Microalgae," ACS Symposium Series; American Chemical Society, 1994, pp. 255-270.
Kureshy et al., "Effect of Ozone Treatment on Cultures of *Nannochloropsis oculata, Isochrysis galbana,* and *Chaetoceros gracilis*," Journal of the World Aquaculture Society, 1999, 30(4), pp. 473-480.
Csogor et al., "Light Distribution in a Novel Photobioreactor-Modelling for Optimization," Journal of Applied Phycology, vol. 13, pp. 325-333, 2001.
Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.
Zittelli et al., "Mass Cultivation of *Nannochloropsis* Sp. In Annular Reactors," Journal of Applied Phycology, vol. 15, pp. 107-113, Mar. 2003.
Strzepek et al., "Photosynthetic Architecture Differs in Coastal and Oceanic Diatoms," Nature, vol. 431, pp. 689-692, Oct. 2004.
Lee et al., "Isolation and Characterization of a Xanthophyll Aberrant Mutant of the Green Alga *Nannochloropsis oculata*," Marine Biotechnology, 2006, vol. 8, pp. 238-245.
International Search Report mailed Sep. 16, 2009 for Application No. PCT/US2009/004296, filed Jul. 24, 2009.
Written Opinion of the International Searching Authority mailed Sep. 16, 2009 for Application No. PCT/US2009/004296, filed Jul. 24, 2009.
Office Action mailed Nov. 14, 2012 in China Patent Application No. 200980138072.X, filed Jul. 24, 2009.
Official Action mailed Jul. 10, 2012 in Mexico Patent Application No. MX/a/2011/000934, filed Jul. 24, 2009.
Official Action mailed Mar. 5, 2013 in Mexico Patent Application No. MX/a/2011/000934, filed Jul. 24, 2009.
Duarte et al., "Glyphosate (GP) Effects with Emphasis on Aquatic Organisms," Colunbia Orinoquia, ISSN: 0121-3709, pp. 70-100, 2004.
Technical Card: Glyphosate, Document filed for the Pesticide Action Network and the Alternatives Thereof, for Latin America (RAP-AL)-Communications and Administration Office, Apr. 2008.

Department of Environment, Housing and Territorial Development Ministry, Resolution (1009), published Jun. 17, 2008.
Examination Report mailed Feb. 20, 2013 in Australian Application No. 2009274500 filed Jul. 24, 2009.
Notice on the Second Office Action mailed Sep. 24, 2013 in Chinese Application No. 200980138072.X filed Jul. 24, 2009.
Zuo-Xi Ruan et al., Effects of Acute Glyphosate Exposure on the Growth and Physiology of *Nostoc sphaeroides*, an Edible Cyanobacterium of Paddy Rice Fields, Acta Hydrobiologica Sinica, Jul. 2008 vol. 32, No. 4.
Genbank Accession No. U71602 (*Nannochloropsis* sp. Violaxanthing/chlorophyll a binding protein precursor (NANVCP) mRNA, 1996.
Sukenik et al. "Characterization of a Gene Encoding the Light-Harvesting Violaxanthin-Chlorophyll Protein of *Nannochloropsis* Sp. (Eustigmatophyceae)," Journal of Phycology, Jun. 2000; 36(3), pp. 563-570.
Abe et al., AG610981, *Musmusculus* molossinus DNA, 2004.
Kopczynski et al., CO268749, *Drosophila melanogaster* cDNA clone EK092604, 2004.
Shi et al., "Analysis of Expressed Sequence Tags from the Marine Microalga *Nannochloropsis oculata* (eustigmatophyceae)," Journal of Phycol, vol. 44, pp. 99-102, 2008.
Thiel et al., "Transformation of a Filamentous Cyanobacterium by Electroporation," Journal of Bacteriology, Oct. 1989, vol. 171, No. 10, pp. 5743-5746.
Krienitz et al., "*Nannochloropsis limnetica* (Eustigmatophyceae), a new species of picoplankton from freshwater," Phycologia, 2000, vol. 39, No. 3, Abstract.
Sukenik et al., "Regulation of Fatty Acid Composition by Irradiance Level in the Eustigmatophyte *Nannochloropsis*," Journal of Phycol., 1989, vol. 25, pp. 686-692.
Rocha et al., "Growth Aspects of the Marine Microalga *Nannochlorpsis gaditana*," Biomolecular Engineering, 2003, vol. 20, pp. 237-242.
MacIntyre et al., "Primary Production by Suspended and Benthic Microalgae in a Turbid Estuary: Time-Scales of Variability in San Antonio Bay, Texas," Marine Ecology Progress Series, 1996, vol. 145, pp. 245-268.
Dunahay et al, "Manipulation of Microalgal Lipid Production Using Genetic Engineering," Applied Biochemistry and Biotechnology, 1996, vol. 57/58/.
Geng et al, "Construction of a System for the Stable Expression of Foreign Genes in *Dunaliella Salina*," Acta Botanica Sinica 46(3): 342-346, 2004.
Chen et al., "Highly Efficient Expression of Rabbit Neutrophil Peptide-1 gene in *Chlorella* Ellipsoidea Cells," Current Genetics 39(5-6): 365-370, 2001.
Suga et al., "Control by Osmolarity and Electric Field Strength of Electro-Induced Gene Transfer and Protein Release in Fission Yeast Cells," Journal of Electrostatics 64(12): 796-801, 2006.
International Search Report and Written Opinion of the International Searching Authority mailed Oct. 30, 2009 for Application No. PCT/US2009/046656, filed Jun. 8, 2009.
International Search Report and Written Opinion of the International Searching Authority mailed Aug. 12, 2009 for Application No. PCT/US2009/003819, filed Jun. 25 2009.
International Search Report and Written Opinion of the International Searching Authority mailed Dec. 20, 2010 for Application No. PCT/US2010/053265, filed Oct. 19, 2010.
Extended European Search Report mailed Mar. 19, 2013 in European Patent Application 10825551.4, filed on Oct. 19, 2010.
Minoda et al., "Improvement of Culture Conditions and Evidence for Nuclear Transformation by Homologous Recombination in a Red Alga, *Cyanidioschyzon merolae* 10D," Plant and Cell Physiology, vol. 45, No. 6, Jun. 2004, pp. 667-671.
Hallmann et al., "Gene Replacement by Homologous Recombination in the Multicellular Green Alga, *Volvox carteri*," Proceedings of the National Academy of Sciences in the United States of America, vol. 94, No. 14, 1997, pp. 7469-7474.

(56) References Cited

OTHER PUBLICATIONS

Kilian et al., "High-efficiency homologous recombination in the oil-producing alga *Nannochloropsis* sp.," Proceedings of the National Academy of Sciences of the United States of America, vol. 108, No. 52, Dec. 2001, pp. 21265-21269.

Extended European Search Report mailed Oct. 19, 2011 in European Patent Application 09759628.2, filed on Jun. 8, 2009.

Hallmann, "Algal Transgenics and Biotechnology," Transgenic Plant Journal, Global Science Books Ltd., GB, vol. 1, No. 1, Jan. 2007, pp. 81-98.

International Search Report and Written Opinion of the International Searching Authority mailed Oct. 20, 2010 for Application No. PCT/US2010/001754, filed Jun. 16, 2010.

International Search Report and Written Opinion of the International Searching Authority mailed Sep. 9, 2009 for Application No. PCT/US2009/046650, filed Jun. 8, 2009.

International Search Report and Written Opinion of the International Searching Authority mailed Jun. 15, 2011 for Application No. PCT/US2010/042666, filed Jul. 20, 2010.

Pollock, "High Carbon Dioxide Requiring Mutants of *Chlamydomonas reinhardtII*," Created Dec. 2003, [online, retrieved Oct. 14, 2010] <http://etd.lsu.edu/docs/available/etd-0828103-114026/unrestricted/Pollock_dis.pdf>.

Drocourt: GenBank Accession No. X52869.1, created Jan. 3, 1995.

Pan: GenBank Accession No. EE109892.1, created Jun. 23, 2008.

Pan: GenBank Accession No. EE109907, created Jun. 23, 2008.

Henriquez et al.: GenBank Accession No. Q07CY9, created Oct. 31, 2006.

International Search Report and Written Opinion of the International Searching Authority mailed Oct. 16, 2012 for Application No. PCT/US2012/035633, filed Apr. 27, 2012.

Yu et al., "Construction and characterization of a normalized cDNA library of *Nannochloropsis oculata* (Eustigmatophyceae)," Chinese Journal of Oceanology and Limnology, vol. 28, No. 4, pp. 802-807, 2010.

Lumbreras et al., "Efficient Foreign Gene Expression in *Chlamydomonas reinhardtii* Mediated by an Endogenous Intron," The Plant Journal, vol. 14, No. 4 Jan. 1, 1998, pp. 441-447, XP001150496, ISN: 0960-7412, DOI: 10.1046/j.1365-313X.1998.00145.X.

Rose A.B., "Intron-Mediated Regulation of Gene Expression," Current Topics in Microbiology and Immunology vol. 326, Jan. 1, 2008, pp. 277-290, XP009145370, ISSN: 0070-217X.

Rose A.B., "The Effect of Intron Location on Intron-Mediated Enhancement of Gene Expression in *Arabidopsis*," The Plant Journal, vol. 40, No. 5, Dec. 1, 2004, pp. 744-751, XP55029911, ISSN: 0960-7412, D0I:10.1111/j.1365-313X.2004.02247, 2004.

International Search Report and Written Opinion of the International Searching Authority mailed Sep. 13, 2013 in Application No. PCT/US2013/038939 filed Apr. 30, 2013.

Notice on the First Office Action mailed May 20, 2013 in Chinese Application No. 201080058106.7 filed Oct. 19, 2010.

Examination Report mailed Apr. 29, 2013 in European Application No. 09759628.2 filed Jun. 8, 2009.

Examination Report mailed Aug. 29, 2013 in Australian Application No. 2009255947 filed Jun. 8, 2009.

Examination Report mailed Sep. 19, 2013 in Australian Application No. 2010310765 filed Oct. 19, 2010.

* cited by examiner

FIG. 1

CLUSTALW alignment of *Chlamydomonas reinhardtii* AOX1 and *Arabidopsis thaliana* AOX1A with the AOX ortholog in W2

FIG. 2

TargetP1.1 prediction for W2 AOX

| Name | Len | cTP | mTP | SP | other | Loc | RC | TPlen |
|---|---|---|---|---|---|---|---|---|
| W2_AOX | 359 | 0.067 | 0.920 | 0.021 | 0.013 | M | 1 | 62 |

5'...atgaagccggaggaggagacacctgcccgattgccgaatgccaccaatcccaggaaggttgccgtggaggagagcttgcgtgacgggccccgttccatcgtgcactttcaagctgagccccaactgccatgcccct
aacgtgcccaaactgaccccgaaagagaaggatctggaaaaacctaccaccacagcgtctggaccaaggaagagcgttcagatcacgcattcccaccagcggattgacctccgggtcgttatg
gcctagcagcaaacccttccggttcagttcgacttgttgccgagcttcaaatacccgcaaggctactgaggatgttcctgaacgtgtgtatttcctcgagaccgtggtcttttttctctgtacctgatcaatcca
agatttgccatcgccctgttgtcatcgaggaggagtgccgttaagcagtccatgcgtacacgtacacgtgaggatgccgagatgccatctcctcggccatcgcgtcgtagaggagcagtaccg
gctagttcctgatgccactctccgacgtccactgctgccgatccgccaaggatgaggccacgtcacgtacgtgaagttaccacaccttgcaagcagtgacgagacgaacgatgacacccttcctgcagaggagcagtaccg
cggccaagtggagatgcataaccccacggctaaggtgctggagcgtcggagaagaagatggcgtaa...3'

SEQ. ID. NO. 1
FIG. 8

MKPEEDTAPIADATNPRKAAVEESLRDGARSIVHFKLSPNRHALMVPKLDPKEKIWENPTHHSVWTKEEVESVQDTHLPPADWTSRVAYGLAQTLRFSFDLLAGFKHRKAT
EDMFLNRVVFLETVAVFFLSYLINPKICHRLVGHEEEAVKTYHIDMMDAGELPLFNHIJPPHAVSYWKLAPDATFRDLILAIRKDEATHREVNHTFASMDENDDNPFLAE
EQYRAQVEMHNSTAMTSEKEKNKMA

SEQ. ID. NO. 2
FIG. 9

DNA sequence for insert comprised of VCP promoter, Ble gene, 3' untranslated region of VCP gene gtttcttgtaccacgccgttaagcaagacggaacaagatggcacgcgtctgcaacagaccggctcgcgccgaacgtgcctcctgctttcaacgatcctgcgaggtcaaccaggatttgctc
gccgggacgatttcatccccttatcaacgagcccttgaggctccaggcgtgcttccacaccccagttggtaacaggacattggggcatcttgcctatcttgtcttagtgccgaaagcctcaac
gacctcccatggggtctgctcaacgcctcaaccttgcagtaaggatccccgagggcaagacccgcaaagcctttctgtcgtcggacaaagcggagcgagggaacaggctcagctcaaccc
tcttgagagcccataagtgcccctgatctatcttcaacagtctttccctgtcacaagaaaacccagctagttgaccaagttgctagagctgatacctgtacttcgctctttgtgtgctttacct
gattggacatggacagacctccccttgctcttccttctaggagcctgggctctcgctcttgttctttcgagagacctttcccttgagttgcgtatccagcgatcaagtatgaagagtgctttcaaa
cctagatacgttctgcccagttctcttgcccttttccacacgtgctcccatcttcacacgactcgcaccatacccgacgaaaccccctcaaaacatcgcaacacttacatcccgctcgtgtcca
accccgatgccatatcctctacagcagcagcaccaccaccaccacttcttaagt

SEQ. ID. NO. 3
FIG. 10 atggccaagttgaccagtgccgttccggtgctcaccgcgcgcgacgtcgccggagcggtcgagttctggaccgaccggctcgggttctcccgggacttcgtggaggacgacttcgccggtg
tggtccgggacgacgtgaccctgttcatcagcgcggtccaggaccaggtggtgccggacaacaccctggcctgggtgtgggtgcgcggcctggacgagctgtacgccgagtggtcggag
gtcgtgtccacgaac

SEQ. ID. NO. 4
FIG. 11 ttccgggacgcctccgggccggccatgaccgagatcggcgagcagccgtggggggcgggagttcgccctgcgcgacccggccggcaactgcgtgcacttcgtggccgaggagcaggact
aagcttctggggaagagccagtggtagtagcagtagcagcagcagtagcagccgcagcactcagtgttggcgcgagagattgtccatcccttcttaacctaccggaagagaaataaggcc
tttctcccgtagctgtcttcgtttgtttgtgctgattgcttgatatgagagtgttgaattcctgcatcatgtttttctctgtagtcctttcctacccccgtcatttttcttttctccctggttcttcttttgtca
cccttatttacataaaatttttctttgtttatagtgagaggaaggtagagaggggaaaacaagaacaacgaacgcaagcgtgtgaaaggagggcgagtagaagagaaacagatctgttg
agcattgagagtggagccgggggaaaggcttgtgtgttgtctttgaaaaagttgtttaaatcacgaatccgttagttctcatgtgtacctctttcactacatgtgatggagaaaacaaaagtg
tgaggattaattgaagaaaaagaagagttcgacacgtcaaaccgcccaaaagacgtcacaaagagaacttgattctctttgccgtgttgatcctgctttttcccccagctttttcttgccaccc
gtggcacacgagatggacaagatcagcacgagcgagtaagggaaga

SEQ. ID. NO. 5
FIG. 12

US 8,709,765 B2

MANIPULATION OF AN ALTERNATIVE RESPIRATORY PATHWAY IN PHOTO-AUTOTROPHS

CROSS-REFERENCE TO RELATED APPLICATIONS

The present application claims the benefit and priority of U.S. Provisional Patent Application Ser. No. 61/227,026 filed on Jul. 20, 2009, titled "Manipulation of an Alternative Respiratory Pathway in Photo-Autotrophs," the disclosure of which is hereby incorporated by reference.

The present application by reference incorporates in entirety the following applications: U.S. Non-Provisional patent application Ser. No. 12/581,812 filed on Oct. 19, 2009, titled "Homologous Recombination in an Algal Nuclear Genome," U.S. Non-Provisional patent application Ser. No. 12/480,635 filed on Jun. 8, 2009, issued on Nov. 27, 2012 as U.S. Pat. No. 8,318,482 and titled "VCP-Based Vectors for Algal Cell Transformation," and U.S. Non-Provisional patent application Ser. No. 12/480,611 filed on Jun. 8, 2009, issued on Feb. 21, 2012 as U.S. Pat. No. 8,119,859 and titled "Transformation of Algal Cells."

REFERENCE TO SEQUENCE LISTINGS

The present application is filed with sequence listing(s) attached hereto and incorporated by reference.

BACKGROUND OF THE INVENTION

Field of the Invention

This invention relates to molecular biology, and more specifically, to the expression of exogenous DNA elements in algal cells and/or the mutation of algal cells.

SUMMARY OF THE INVENTION

Exemplary methods for increasing TAG production in an algal cell during imbalanced growth conditions are provided. Some methods comprise knocking out an AOX gene, wherein the AOX gene produces an amino acid sequence having substantial similarity to the amino acid sequence of SEQ. ID. NO. 2. In further methods, the algal cell may be of genus Nannochloropsis. The AOX gene may be replaced by a construct having a nucleotide sequence having substantial similarity to SEQ ID. NOS. 3 through 5 (inclusive), wherein each of the sequences are next to or in close proximity to one another in a linear fashion. In some methods, the AOX gene may be replaced via homologous recombination. Further, the AOX gene may have a nucleotide sequence with substantial similarity to SEQ ID. NO. 1. Additionally, the recombinant algal cell may be grown in the presence of an antibiotic in which the selected recombinant algal cell is resistant. A marker gene may confer resistance to zeocine. As a result, lipid production by the selected recombinant algal cell may be increased over that produced by a wild-type algal cell.

DETAILED DESCRIPTION OF THE INVENTION

Whole chain electron transport in mitochondrial respiration typically involves four major protein complexes located in the inner mitochondrial membrane. During respiratory electron flow through these four complexes, electron donors, such as nicotinamide adenine dinucleotide phosphate (NADP), and succinate, become oxidized, while molecular oxygen ultimately becomes reduced by the terminal protein complex in the pathway known as cytochrome c oxidase. Respiratory electron flow is coupled to proton pumping across the mitochondrial inner membrane, generating a significant proton motive force (PMF). The PMF is subsequently released through the adenosine triphosphate (ATP) synthase, leading to the generation of energy rich molecular ATP.

A second form of respiratory electron flow, known as the alternative respiratory pathway, employs an oxidase known as the alternative oxidase (AOX), which is generally located upstream to the cytochrome c oxidase in the respiratory pathway. The alternative respiratory pathway terminates electron flow with the reduction of molecular oxygen upstream of complex III, therefore bypassing this complex as well as the terminal cytochrome c oxidase. Since complex III and the cytochrome c oxidase pump protons during electron transport, alternative respiration leads to the formation of significantly less ATP per electron donor oxidized, relative to whole chain respiration. In this respect, alternative respiration is a wasteful process in terms of maximizing energy conversion from cellular reductant. For oxygenic photo-autotrophs, it may be necessary to employ such a wasteful pathway during imbalanced growth, when more reduced carbon is generated through photosynthesis than can be used for growth and cell division. Examples of imbalanced growth include excessive irradiance and low nutrient status. The accumulation of excess reduced carbon during imbalanced growth may also be alleviated through the generation of triacylglycerides (TAGs).

According to various exemplary embodiments herein, the loss of reductant through an alternative respiratory pathway that generally exists in wild type strains of various photo-autotrophs, such as marine algae, is restricted and/or eliminated by generating an oxidase deletion strain.

Figure 1:
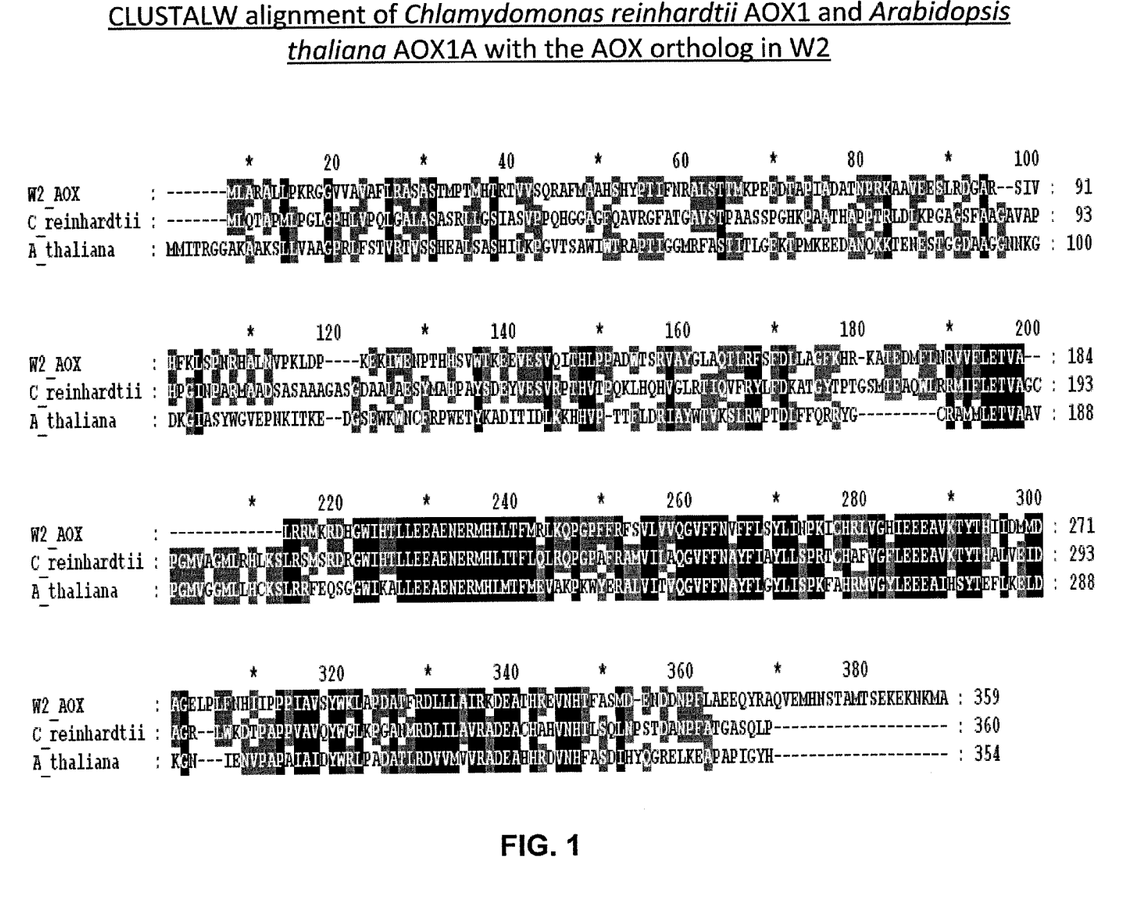
FIG. 1 shows an exemplary CLUSTALW alignment for three amino acids produced by various AOX genes, as found in three different types of algae.
Figure 8:
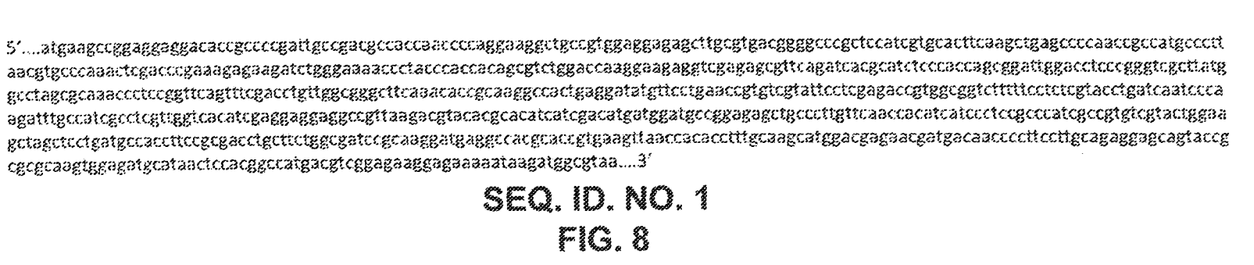
FIG. 8 SEQ. ID. NO. 1 is an exemplary nucleotide sequence for the AOX gene sequence.
Figure 9:
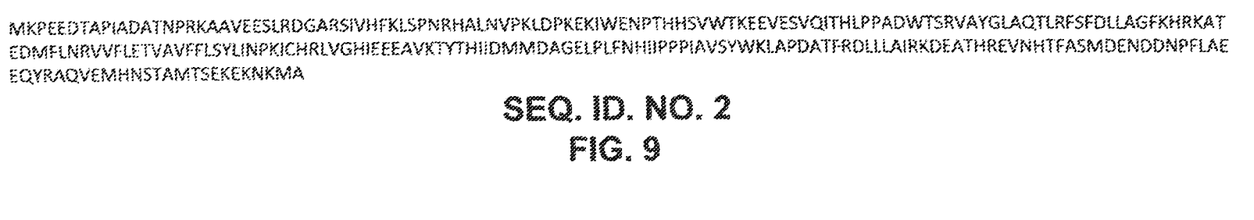
FIG. 9 SEQ. ID. NO. 2 is an exemplary amino acid sequence for the amino acid produced by SEQ. ID. NO. 1.
Figure 10:
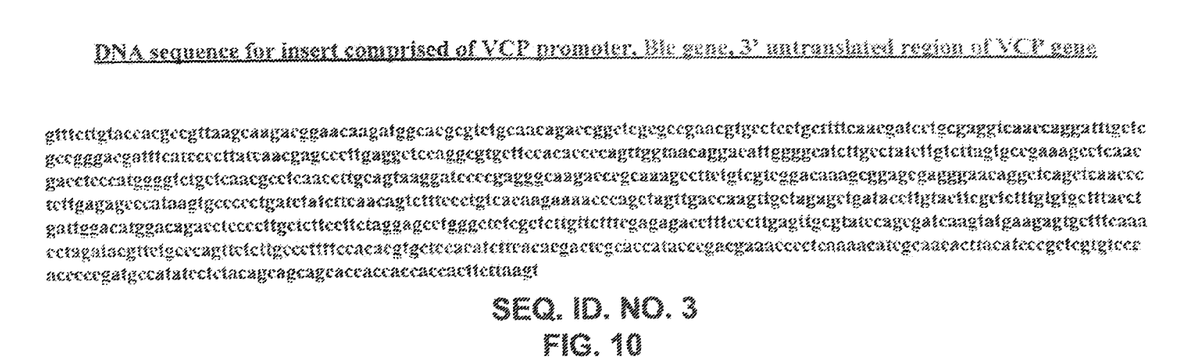
FIG. 10 SEQ. ID. NO. 3 is an exemplary nucleotide sequence for a VCP promoter gene.
Figure 11:
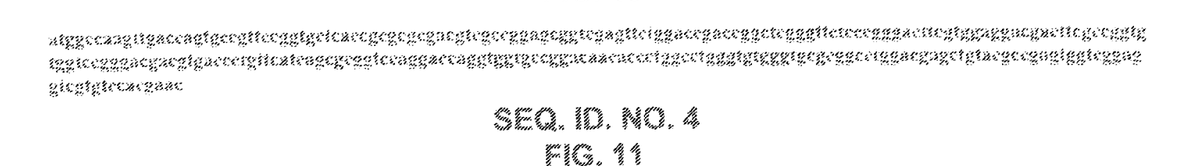
FIG. 11 SEQ. ID. NO. 4 is an exemplary nucleotide sequence for a ble marker gene (confers resistance to zeocine).
Figure 12:
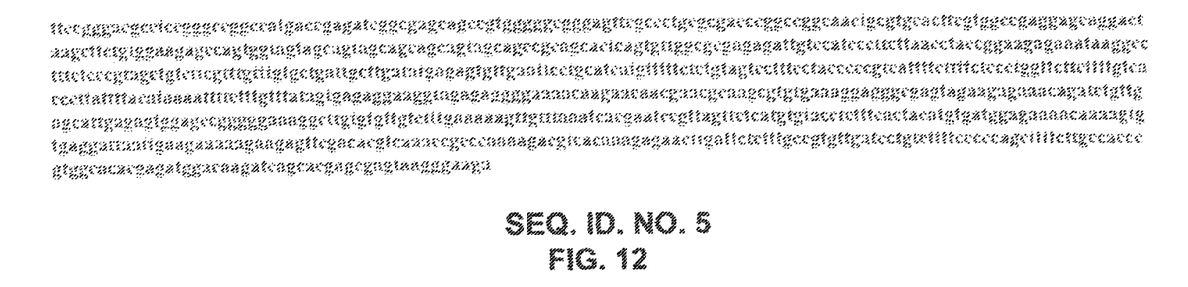
FIG. 12 SEQ. ID. NO. 5 is an exemplary nucleotide sequence for a 3' UTR gene.

FIG. 1 shows an exemplary CLUSTALW alignment for three amino acids produced by various AOX genes, as found in three different types of algae. CLUSTALW is a general purpose multiple sequence alignment program for DNA or proteins. Shown in FIG. 1 is an amino acid sequence alignment for two amino acids produced by two well-characterized AOX genes, as found in *Chlamydomonas reinhardtii* and *Arabidopsis thaliana*, with the *Chlamydomonas reinhardtii* having the AOX1 gene sequence, and the *Arabidopsis thaliana* having the AOX1A gene sequence. Also shown in FIG. 1 is the amino acid sequence produced by wild-type *Nannochloropsis* (W2), having the AOX gene sequence. SEQ. ID. NO. 1 is an exemplary nucleotide sequence for the AOX gene sequence. SEQ. ID. NO. 2 is an exemplary amino acid sequence for the amino acid produced by SEQ. ID. NO. 1. The close similarity of the two well-characterized amino acid sequences to the amino acid sequence produced by the wild-type *Nannochloropsis* AOX gene sequence confirms the identity of the *Nannochloropsis* AOX gene sequence.

Figure 2:
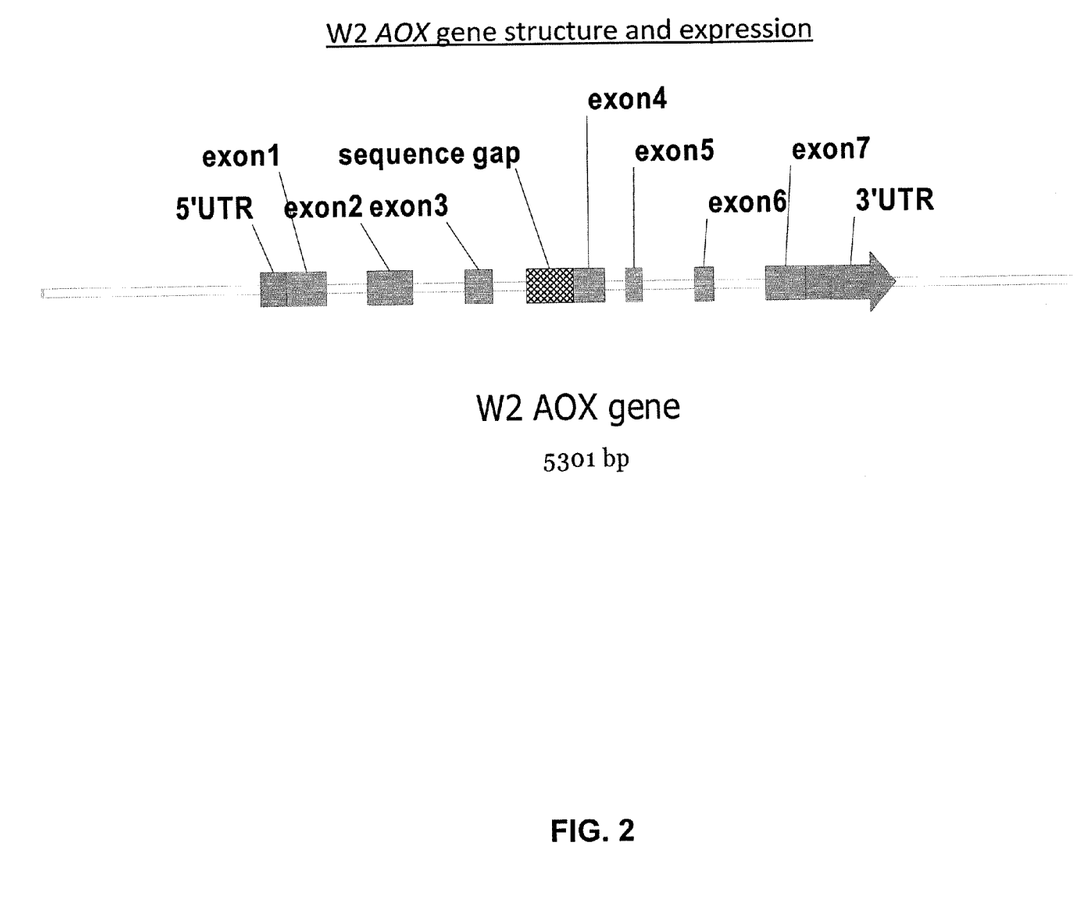
FIG. 2 shows an exemplary gene structure and expression diagram for the wild-type Nannochloropsis (W2) AOX gene sequence, as found in the Nannochloropsis genome.

FIG. 2 shows an exemplary gene structure and expression diagram for the wild-type *Nannochloropsis* (W2) AOX gene sequence, as found in the *Nannochloropsis* genome. In FIG. 2, the exemplary gene structure and expression diagram is comprised of seven exons, including a 5' untranslated region (5'UTR), a 3' untranslated region (3'UTR), various introns between the exons, and a sequence gap. In total, the wild-type *Nannochloropsis* (W2) AOX gene sequence of FIG. 2 represents approximately 5,301 base pairs (bp). The exemplary gene structure of FIG. 2 exists in the genome of the wild-type *Nannochloropsis* (W2). Prior to translation, the introns are spliced out, to form the exemplary AOX gene sequence comprising the 5' UTR, exon1 through exon7 (inclusive), and the 3' UTR.

Figure 3:
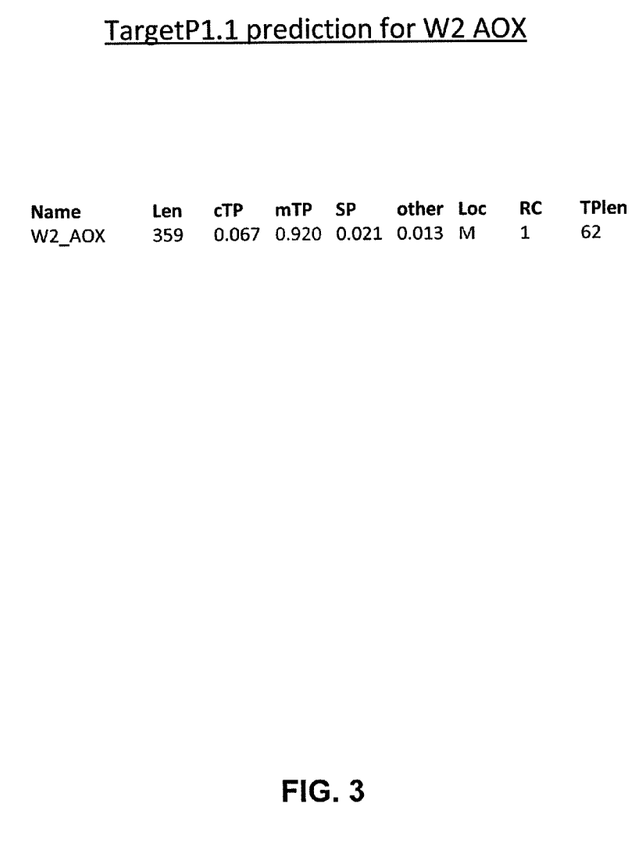
FIG. 3 shows exemplary TargetP1.1 prediction data for the wild-type Nannochloropsis (W2) AOX gene sequence.

FIG. 3 shows exemplary TargetP1.1 prediction data for the wild-type *Nannochloropsis* (W2) AOX gene sequence. TargetP1.1 is software that predicts the subcellular location of eukaryotic protein sequences. The assignment is based on the predicted presence of the following N-terminal presequences: chloroplast transit peptide (cTP), mitochondrial targeting peptide (mTP), and/or secretory pathway signal peptide (SP). For each input sequence (such as the AOX gene sequence), the following may be printed: Name (sequence name truncated to 20 characters), Len (sequence length), and/or Loc (prediction of localization, based on the scores). The Loc codes may be: C: chloroplast, i.e. the sequence contains cTP, a chloroplast transit peptide; M: mitochondrion, i.e. the sequence contains mTP, a mitochondrial targeting peptide; S: secretory pathway, i.e. the sequences contains SP, a signal peptide; and/or other: any other location. RC indicates reliability class, from 1 to 5, where 1 indicates the strongest prediction. As shown in FIG. 3, the wild-type *Nannochloropsis* (W2) AOX gene sequence appears to be targeted to the mitochondrion.

Figure 4:
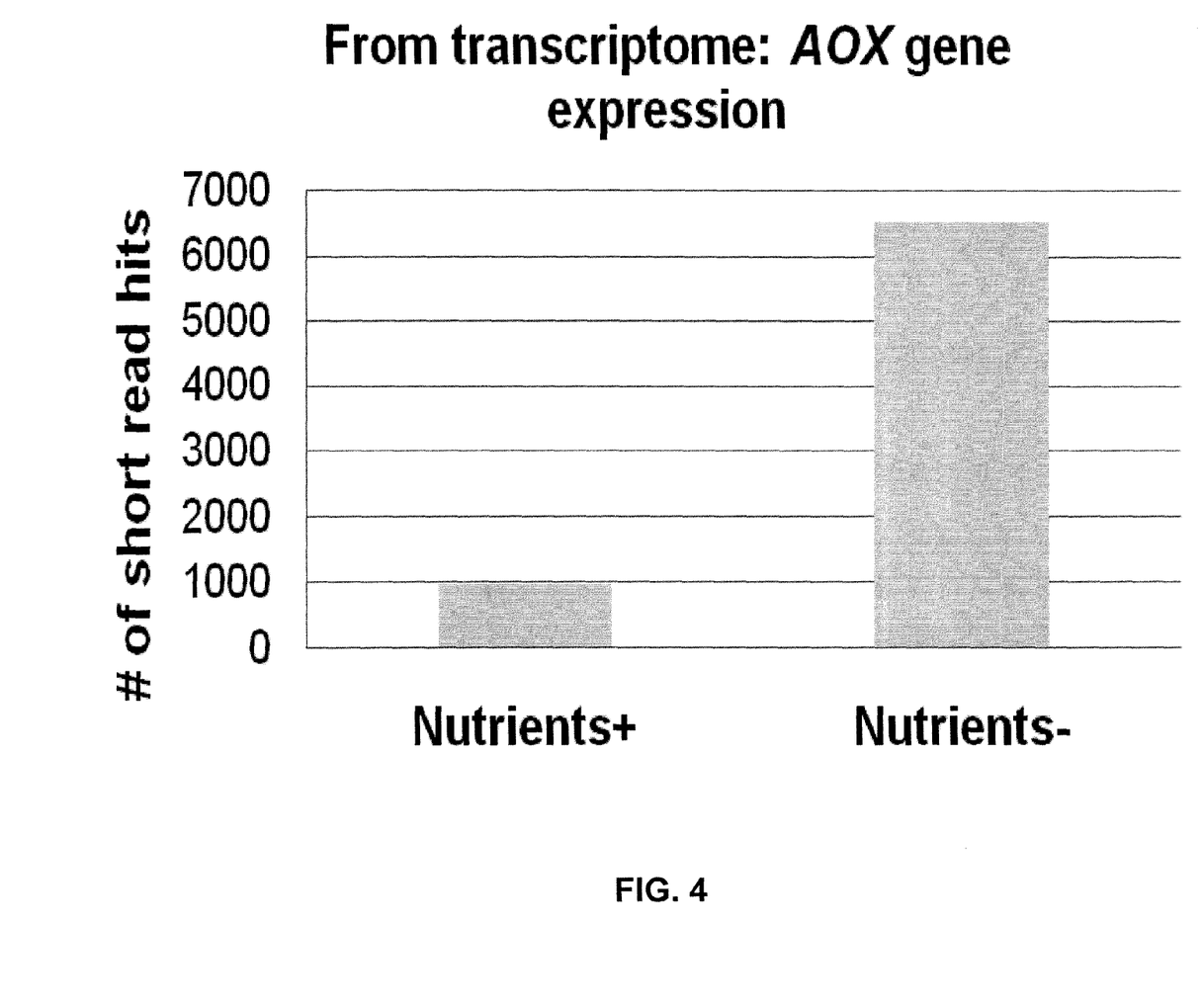
FIG. 4 shows a chart reflecting exemplary expression levels of the wild-type Nannochloropsis (W2) AOX gene sequence in the presence and absence of nutrients, labeled as (Nutrients+) and (Nutrients−), respectively.

FIG. 4 shows a chart reflecting exemplary expression levels of the wild-type *Nannochloropsis* (W2) AOX gene sequence in the presence and absence of nutrients, labeled as (Nutrients+) and (Nutrients−), respectively. According to various exemplary embodiments, the wild-type *Nannochloropsis* (W2) AOX gene sequence is expressed at reduced rates during balanced growth (e.g. balanced in terms of nutrients and/or illumination), and is up-regulated during imbalanced growth (e.g. following nutrient starvation and/or high illumination). During imbalanced growth, a portion of environmental carbon (e.g. $CO_2$) is consumed by wild-type *Nannochloropsis* and is retained in the form of triacylglyceride (TAG). At the same time, *Nannochloropsis* is unable to retain other environmental carbon in the form of TAG and instead releases it in the form of carbon dioxide ($CO_2$) by way of the alternative respiratory pathway, facilitated by the AOX gene sequence.

Figure 5:
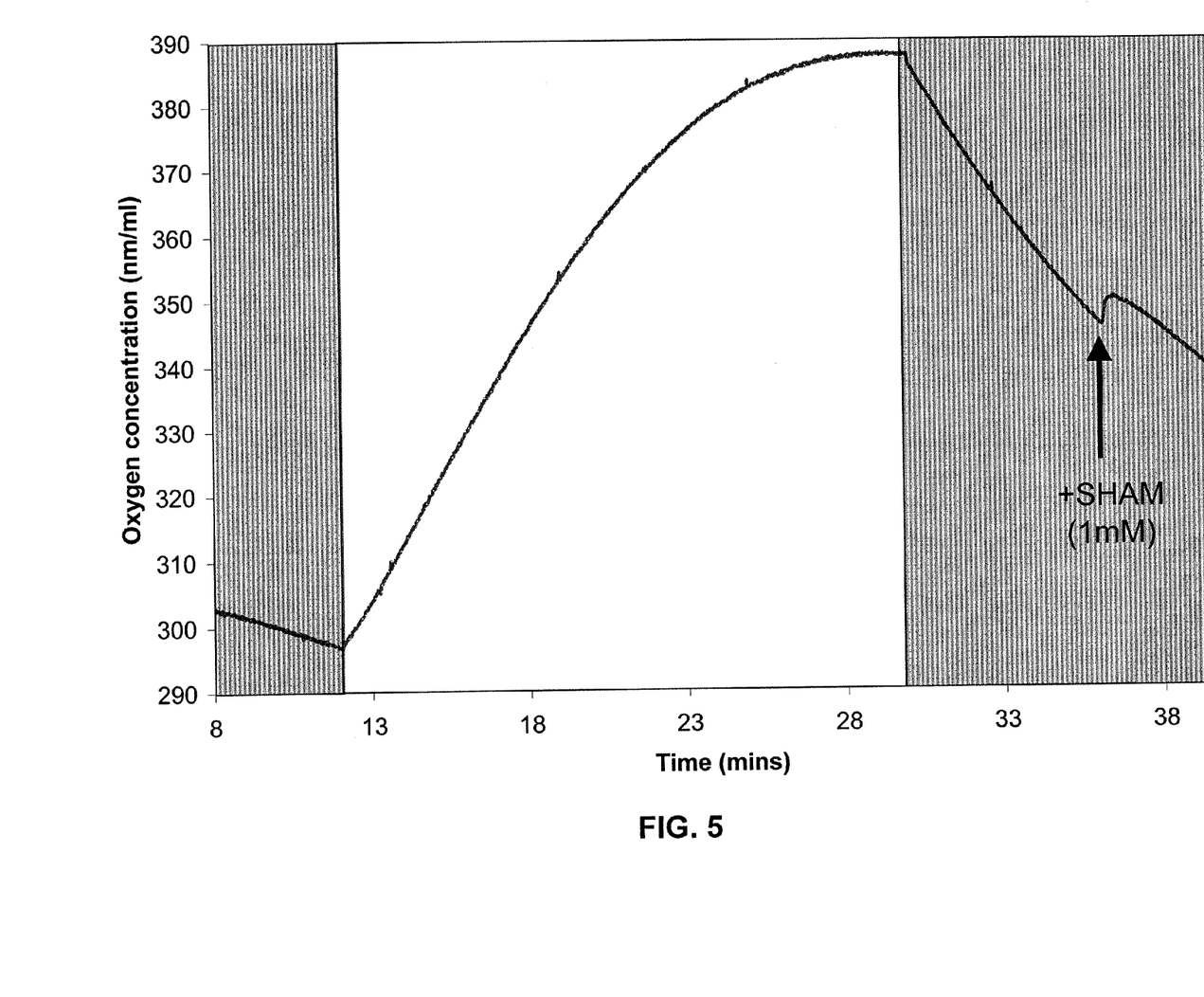
FIG. 5 shows a chart reflecting exemplary environmental oxygen concentrations in the presence of wild-type Nannochloropsis under varying light conditions over time.

FIG. 5 shows a chart reflecting exemplary environmental oxygen concentrations in the presence of wild-type *Nannochloropsis* under varying light conditions over time. In the chart of FIG. 5, periods of darkness are shaded; periods of light are not shaded. Exposure of *Nannochloropsis* to excessive illumination results in stimulation of respiration, a significant proportion of which may be eliminated using the AOX specific inhibitor salicylhydroxamic acid (SHAM). Since AOX activity is generally a pathway that eliminates cellular reductant in a wasteful manner, eliminating AOX activity may lead to an increased accumulation of reduced carbon in the form of either cellular components, resulting in higher rates of productivity, or as storage components, resulting in increased rates of TAG accumulation. As shown in the chart of FIG. 5, the introduction of 1 millimolar (mM) SHAM results in a decrease in the rate of oxygen consumption, evidencing the influence of the increased activity of the AOX protein on the alternative respiratory pathway of *Nannochloropsis*.

Figure 6:
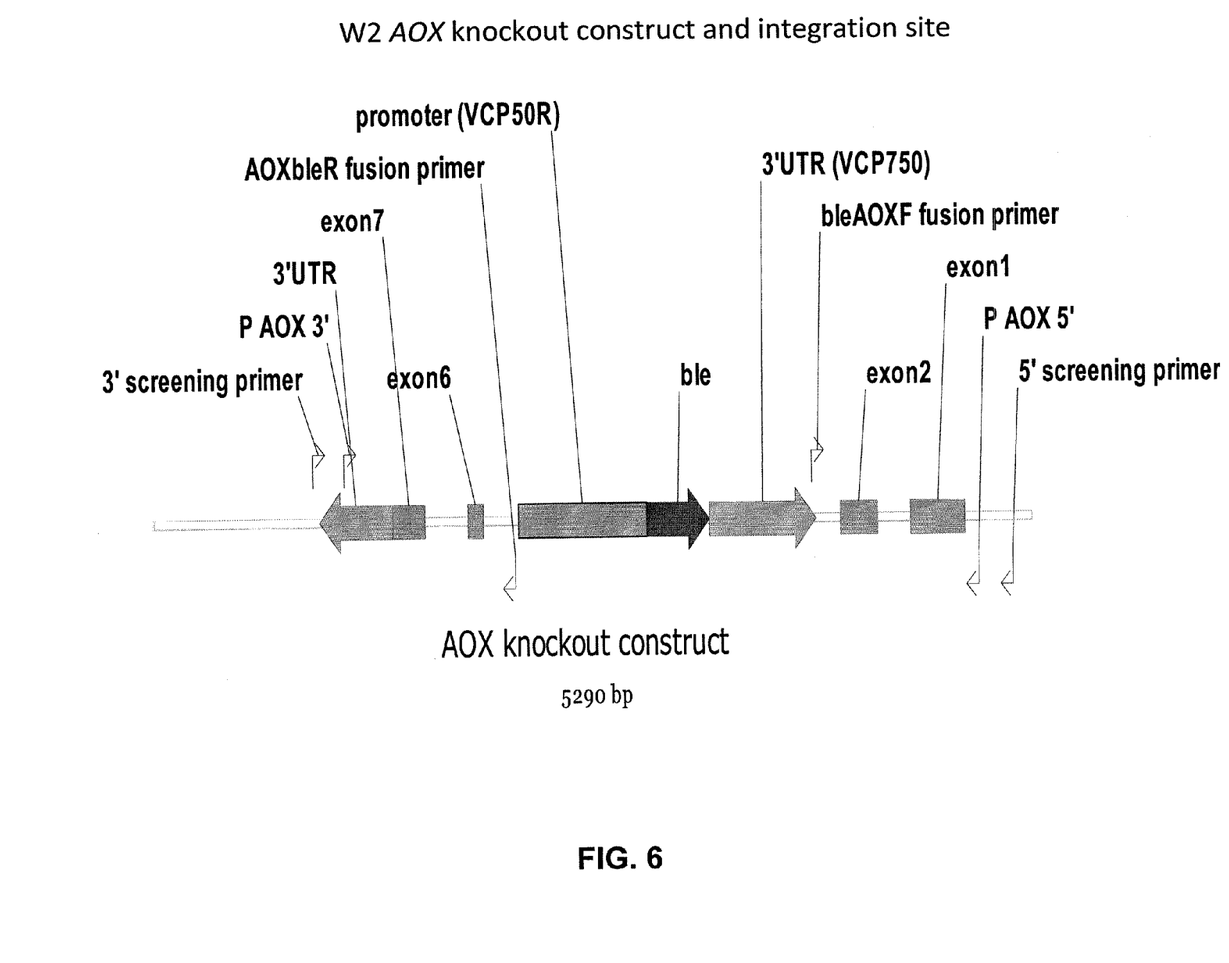
FIG. 6 shows an exemplary W2 AOX knockout construct and integration site.

FIG. 6 shows an exemplary W2 AOX knockout construct and integration site. In order to permanently eliminate AOX activity in marine algae, provide improved growth, and/or facilitate TAG accumulation (e.g. in outdoor pond systems), the inventors generated the exemplary W2 AOX knockout construct as shown and described in connection with FIG. 6 to create a mutant *Nannochloropsis*. Utilizing homologous recombination as described in U.S. Non-Provisional patent application Ser. No. 12/581,812 filed on Oct. 19, 2009, titled "Homologous Recombination in an Algal Nuclear Genome," which is hereby incorporated by reference, the inventors replaced the AOX gene sequence of the wild-type *Nannochloropsis* (W2) with the promoter, ble and 3' UTR genes as illustrated in the W2 AOX knockout construct shown in FIG. 6. Exemplary promoters, ble and 3' UTR genes that may be suitable for such purposes are described in U.S. Non-Provisional patent application Ser. No. 12/480,635 filed on Jun. 8, 2009, titled "VCP-Based Vectors for Algal Cell Transformation," which is hereby incorporated by reference. SEQ. ID. NO. 3 is an exemplary nucleotide sequence for a VCP promoter gene, SEQ. ID. NO. 4 is an exemplary nucleotide sequence for a ble marker gene (confers resistance to zeocine), and SEQ. ID. NO. 5 is an exemplary nucleotide sequence for a 3' UTR gene. SEQ. ID. NOS. 3-5, as a unit, via homologous recombination, may replace the wild-type AOX gene as found in the genome of wild-type *Nannochloropsis*.

Figure 7:
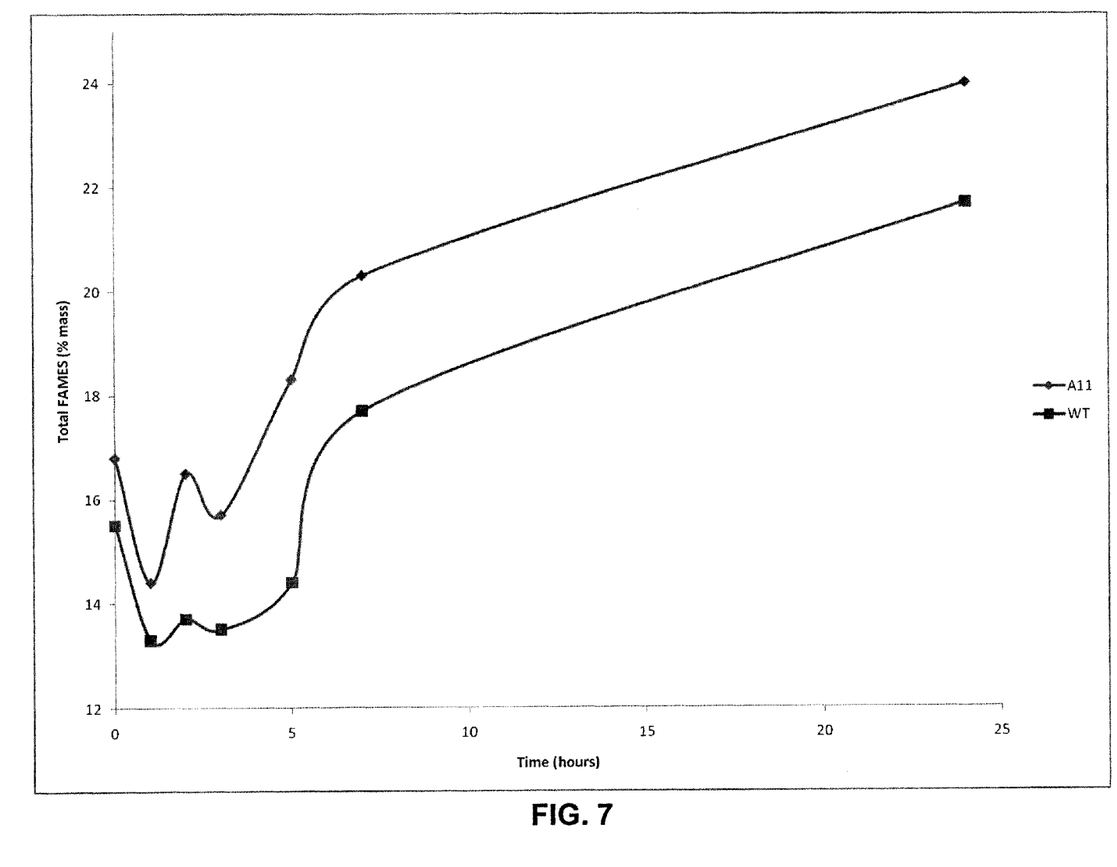
FIG. 7 shows a chart with actual exemplary data comparing the accumulation of fatty acid methyl esters (FAMES) during nutrient starvation of wild-type Nannochloropsis (WT) and mutant Nannochloropsis (A11).

FIG. 7 shows a chart with actual exemplary data comparing the accumulation of fatty acid methyl esters (FAMES) during nutrient starvation of wild-type *Nannochloropsis* (WT) and mutant *Nannochloropsis* (A11). TAGs are a subset of FAMES. The mutant *Nannochloropsis* was constructed per FIG. 6 and the associated description herein. As shown in FIG. 7, the mutant *Nannochloropsis* (A11) accumulates higher amounts of FAMES as a percentage of total mass at all times than the wild-type *Nannochloropsis* (WT).

While various embodiments have been described herein, it should be understood that they have been presented by way of example only, and not limitation. Thus, the breadth and scope of a preferred embodiment should not be limited by any of the herein-described exemplary embodiments.

The invention claimed is:

1. A method for increasing triacylglyceride ("TAG") production in an algal cell during imbalanced growth conditions, the method comprising:
disrupting an alternative oxidase ("AOX") gene, wherein the AOX gene encodes an amino acid sequence comprising the amino acid sequence of SEQ. ID. NO. 2.

2. The method of claim 1, wherein the algal cell is of genus *Nannochloropsis*.

3. The method of claim 1, wherein the AOX gene is replaced by a construct having a nucleotide sequence comprising SEQ ID. NO. 1, SEQ ID. NOS. 3-5.

4. The method of claim 3, wherein the AOX gene is replaced by the construct of claim 4 via homologous recombination.

5. The method of claim 3, wherein the algal cell is grown in presence of an antibiotic to which the algal cell is resistant.

6. The method of claim 3, wherein the marker gene confers resistance to zeocine.

7. The method of claim 3, where the algal cell is grown under imbalanced growth conditions.

8. The method of claim 7, where the algal cell is grown under starvation conditions.

9. The method of claim 3, wherein lipid production is increased over that produced by a corresponding undisrupted wild-type *Nannochloropsis* algal cell.

10. A transformation method for introducing deoxyribonucleic acid (DNA) into a nucleus of an algal cell, the method comprising:
preparing a transformation construct, the transformation construct having a first sequence of DNA similar to a corresponding first sequence of nuclear DNA, the transformation construct having a second sequence of DNA similar to a corresponding second sequence of the nuclear DNA, the transformation construct having a sequence of DNA of interest inserted between the first and second sequences of DNA of the transformation construct, and
transforming a target sequence of DNA inserted between the first and second corresponding sequences of the nuclear DNA, resulting in replacement of the target sequence of DNA with the sequence of DNA of interest, wherein the target sequence comprises SEQ. ID. NO. 1, SEQ ID. NOS. 3-5.

* * * * *

SEQUENCE LISTING

<160> NUMBER OF SEQ ID NOS: 5

<210> SEQ ID NO 1
<211> LENGTH: 753
<212> TYPE: DNA
<213> ORGANISM: Nannochloropsis

<400> SEQUENCE: 1

```
atgaagccgg aggaggacac cgccccgatt gccgacgcca ccaacccccag gaaggctgcc      60
gtggaggaga gcttgcgtga cggggcccgc tccatcgtgc acttcaagct gagccccaac     120
cgccatgccc ttaacgtgcc caaactcgac ccgaaagaga gatctggga aaaccctacc     180
caccacagcg tctggaccaa ggaagaggtc gagagcgttc agatcacgca tctcccacca     240
gcggattgga cctcccgggt cgcttatggc ctagcgcaaa ccctccggtt cagtttcgac     300
ctgttggcgg gcttcaaaca ccgcaaggcc actgaggata tgttcctgaa ccgtgtcgta     360
ttcctcgaga ccgtggcggt cttttttcctc tcgtacctga tcaatcccaa gatttgccat     420
cgcctcgttg gtcacatcga ggaggaggcc gttaagacgt acacgcacat catcgacatg     480
atggatgccg gagagctgcc cttgttcaac cacatcatcc ctccgcccat cgccgtgtcg     540
tactggaagc tagctcctga tgccaccttc cgcgacctgc ttctggcgat ccgcaaggat     600
gaggccacgc accgtgaagt taaccacacc tttgcaagca tggacgagaa cgatgacaac     660
cccttccttg cagaggagca gtaccgcgcg caagtggaga tgcataactc cacggccatg     720
acgtcggaga aggagaaaaa taagatggcg taa                                  753
```

<210> SEQ ID NO 2
<211> LENGTH: 250
<212> TYPE: PRT
<213> ORGANISM: Nannochloropsis

<400> SEQUENCE: 2

```
Met Lys Pro Glu Glu Asp Thr Ala Pro Ile Ala Asp Ala Thr Asn Pro
1               5                   10                  15

Arg Lys Ala Ala Val Glu Glu Ser Leu Arg Asp Gly Ala Arg Ser Ile
            20                  25                  30

Val His Phe Lys Leu Ser Pro Asn Arg His Ala Leu Asn Val Pro Lys
        35                  40                  45

Leu Asp Pro Lys Glu Lys Ile Trp Glu Asn Pro Thr His His Ser Val
    50                  55                  60

Trp Thr Lys Glu Glu Val Glu Ser Val Gln Ile Thr His Leu Pro Pro
65                  70                  75                  80

Ala Asp Trp Thr Ser Arg Val Ala Tyr Gly Leu Ala Gln Thr Leu Arg
                85                  90                  95

Phe Ser Phe Asp Leu Leu Ala Gly Phe Lys His Arg Lys Ala Thr Glu
            100                 105                 110

Asp Met Phe Leu Asn Arg Val Val Phe Leu Glu Thr Val Ala Val Phe
        115                 120                 125

Phe Leu Ser Tyr Leu Ile Asn Pro Lys Ile Cys His Arg Leu Val Gly
    130                 135                 140

His Ile Glu Glu Glu Ala Val Lys Thr Tyr Thr His Ile Ile Asp Met
145                 150                 155                 160

Met Asp Ala Gly Glu Leu Pro Leu Phe Asn His Ile Ile Pro Pro Pro
                165                 170                 175
```

-continued

```
Ile Ala Val Ser Tyr Trp Lys Leu Ala Pro Asp Ala Thr Phe Arg Asp
            180                 185                 190

Leu Leu Leu Ala Ile Arg Lys Asp Glu Ala Thr His Arg Glu Val Asn
        195                 200                 205

His Thr Phe Ala Ser Met Asp Glu Asn Asp Asn Pro Phe Leu Ala
    210                 215                 220

Glu Glu Gln Tyr Arg Ala Gln Val Gly Met His Asn Ser Thr Ala Met
225                 230                 235                 240

Thr Ser Glu Lys Glu Lys Asn Lys Met Ala
            245                 250

<210> SEQ ID NO 3
<211> LENGTH: 795
<212> TYPE: DNA
<213> ORGANISM: Nannochloropsis

<400> SEQUENCE: 3
gtttcttgta ccacgccgtt aagcaagacg gaacaagatg gcacgcgtct gcaacagacc      60
ggctcgcgcc gaacgtgcct cctgcttttc aacgatcctg cgaggtcaac caggatttgc     120
tcgccgggac gatttcatcc ccttatcaac gagcccttga ggctccaggc gtgcttccac     180
accccagttg gtaacaggac attggggcat cttgcctatc ttgtcttagt gccgaaagcc     240
tcaacgacct cccatggggt ctgctcaacg cctcaacctt gcagtaagga tccccgaggg     300
caagacccgc aaagccttct gtcgtcggac aaagcggagc gagggaacag gctcagctca     360
accctcttga gagcccataa gtgccccctg atctatcttc aacagtcttt ccctgtcaca     420
agaaaaccca gctagttgac caagttgcta gagctgatac cttgtacttc gctctttgtg     480
tgctttacct gattggacat ggacagacct ccccttgctc ttccttctag agcctgggc     540 tctcgctctt gttctttcga gagcctttc ccttgagttg cgtatccagc gatcaagtat      600
gaagagtgct ttcaaaccta gatacgttct gcccagttct cttgcccttt tccacacgtg     660
ctccacatct tcacacgact cgcaccatac ccgacgaaac ccctcaaaac atcgcaacac     720
ttacatcccg ctcgtgtccc accccgatg ccatatcctc tacagcagca gcaccaccac      780
caccacttct taagt                                                      795

<210> SEQ ID NO 4
<211> LENGTH: 255
<212> TYPE: DNA
<213> ORGANISM: Nannochloropsis

<400> SEQUENCE: 4
atggccaagt tgaccagtgc cgttccggtg ctcaccgcgc gcgacgtcgc cggagcggtc      60
gagttctgga ccgaccggct cgggttctcc cgggacttcg tggaggacga cttcgccggt     120
gtggtccggg acgacgtgac cctgttcatc agcgcggtcc aggaccaggt ggtgccggac     180
aacaccctgg cctgggtgtg ggtgcgcggc ctggacgagc tgtacgccga gtggtcggag     240
gtcgtgtcca cgaac                                                      255

<210> SEQ ID NO 5
<211> LENGTH: 783
<212> TYPE: DNA
<213> ORGANISM: Nannochloropsis

<400> SEQUENCE: 5
ttccgggacg cctccgggcc ggccatgacc gagatcggcg agcagccgtg ggggcgggag      60
ttcgccctgc gcgacccggc cggcaactgc gtgcacttcg tggccgagga gcaggactaa     120
```

-continued

```
gcttctgtgg aagagccagt ggtagtagca gtagcagcag cagtagcagc cgcagcactc    180
agtgttggcg cgagagattg tccatcccct cttaacctac cggaagagaa ataaggcctt    240
tctcccgtag ctgtcttcgt ttgtttgtgc tgattgcttg atatgagagt gttgaattcc    300
tgcatcatgt ttttctctgt agtcctttcc taccccgtc attttctttt ctccctggtt     360
cttcttttgt caccctatt ttacataaaa ttttctttgt ttatagtgag aggaaggtag     420 agagggaaa acaagaacaa cgaacgcaag cgtgtgaaag gagggcgagt agaagagaaa     480
cagatctgtt gagcattgag agtggagccg ggggaaaggc ttgtgtgttg tctttgaaaa    540
agttgtttaa atcacgaatc cgttagttct catgtgtacc tctttcacta catgtgatgg    600
agaaaacaaa agtgtgagga ttaattgaag aaaaagaaga gttcgacacg tcaaaccgcc    660
caaaagacgt cacaaagaga acttgattct ctttgccgtg ttgatcctgt ctttcccc      720 agcttttctt gccacccgtg gcacacgaga tggacaagat cagcacgagc gagtaaggga    780
aga                                                                 783
```